United States Patent [19]

Casagrande et al.

[11] 4,272,529
[45] Jun. 9, 1981

[54] O-ALCOXYCARBONYLPHENYL ESTERS OF ANTHRANILIC ACID WITH THERAPEUTICAL ACTIVITY, METHOD FOR THEIR PREPARATION AND RELATED PHARMACEUTICAL COMPOSITION

[75] Inventors: Cesare Casagrande, Arese; Giorgio Ferrari, Milan, both of Italy

[73] Assignee: Simes S.p.A., Milan, Italy

[21] Appl. No.: 137,295

[22] Filed: Apr. 3, 1980

[30] Foreign Application Priority Data

Jul. 31, 1979 [IT] Italy ................................ 24806 A/79

[51] Int. Cl.³ ..................... A61K 31/60; C07C 101/54
[52] U.S. Cl. ..................................... 424/230; 560/47; 544/94
[58] Field of Search .................. 560/47; 424/310, 230

[56] References Cited

U.S. PATENT DOCUMENTS

| 3,642,864 | 2/1972 | Wanghisi | 560/47 |
| 3,681,394 | 8/1972 | Sherlock | 560/47 |
| 3,692,818 | 9/1972 | Boltze et al. | 560/47 |
| 3,694,489 | 9/1972 | Boltze et al. | 560/47 |
| 4,091,095 | 5/1978 | Söder | 560/48 |
| 4,153,691 | 5/1979 | Davis et al. | 424/230 |
| 4,217,340 | 8/1980 | Robert | 424/230 |

FOREIGN PATENT DOCUMENTS 904340 7/1922 Canada ................................ 560/47
54-3032 1/1979 Japan .

OTHER PUBLICATIONS

Kato, "Chem. Absts.", 87, 134702(K), 1977.
Ferrer, "Chem. Absts.", 87, 134705(P), 1977.

Primary Examiner—G. T. Breitenstein
Attorney, Agent, or Firm—Cushman, Darby & Cushman

[57] ABSTRACT

The N-m-trifluoromethylphenylanthranilates of O-alcoxycarbonylphenyl, having the formula

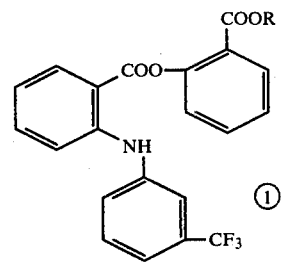

wherein R is an alkyl group, preferably comprising 1 to 4 carbon atoms, besides being of low toxicity, are endowed with anti-inflammatory properties and are adapted for the treatment of inflammatory and thrombotic diseases. The method for the preparation of the above compounds comprises reacting the N-m-trifluoromethylphenylisatoic anhydride with an alkyl salicylate.

7 Claims, No Drawings

O-ALCOXYCARBONYLPHENYL ESTERS OF ANTHRANILIC ACID WITH THERAPEUTICAL ACTIVITY, METHOD FOR THEIR PREPARATION AND RELATED PHARMACEUTICAL COMPOSITION

The present invention relates to esters of flufenamic acid with alkyl salicylates having the formula (1):

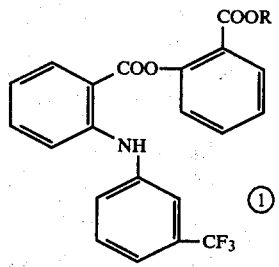

wherein R is an alkyl group, particularly comprising 1 to 4 carbon atoms. The flufenamic acid, having the formula (2),

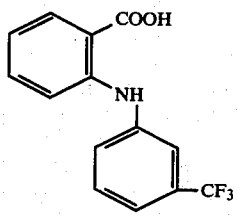

is a well known, non-steroidal anti-inflammatory drug, of the group of phenamates, which are anti-inflammatory substances having the common structure of N-arylanthranilic acids, generally substituted in either or both aromatic systems; the flufenamic acid can be considered as the most studied and the mainly therapeutically used compound of this class of drugs.

Careful studies have been carried out not only on the arylanthranilic acids but also on their esters as regards their pharmacological properties, such as the alkenyl and alkinyl esters (Japanese application No. 53 141233), hydroxy- and alkoxy-alkyl esters (German Pat. No. 1939112), and the esters with geminal diols (U.K. Pat. No. 1199386).

The esters of the present invention constitute a particular group of phenamate esters, in that in only one molecule there are comprised both the structure components of a phenamate, and precisely of the flufenamic acid, and those of a salicylate or, more exactly, of an O-salicylate.

The present invention relates also to a method for the synthesis of the esters of formula (1), wherein the isatoic anhydride corresponding to the flufenamic acid and having the formula (3), is directly reacted with an alkyl salicylate having the formula (4):

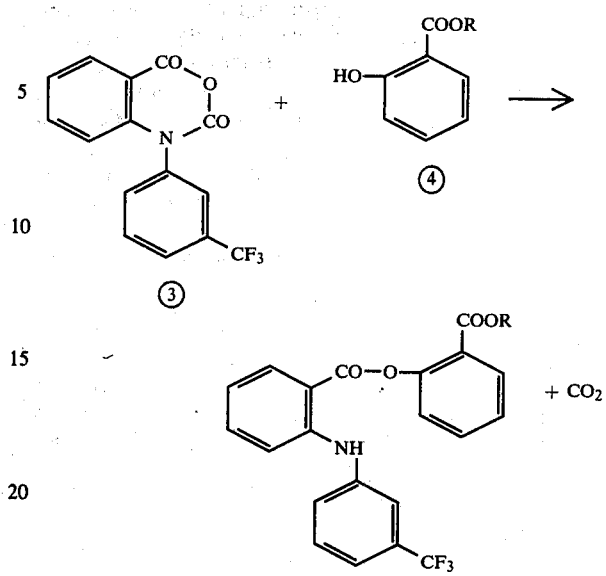

wherein R is an alkyl group, preferably comprising 1 to 4 carbon atoms.

The reaction can be carried out in a suitable, unreactive solvent, or even in an easier way, by direct heating of the reactants, by usefully taking advantage of the properties of low melting point and of good solvent capability of the alkyl salicylates; it can be effected by reacting equimolar amounts of the reacting compounds, or also using an excess of alkyl salicylate; the latter, being readily distillable, can be removed from the reaction mixture and recovered at the end of the reaction.

It has been found that the compounds of the present invention are endowed with particularly favourable pharmacological properties, which are better and unespected with respect to the therapeutical properties of the two starting compounds, as regards their capability of giving the effects of the phenamates, and particularly of the flufenamic acid, in combination with those of the salicylates and acetylsalicylates, whereas at the same time their toxicological properties are improved with respect to both the phenamates and the salicylic derivatives.

For example the acute toxicity per os of the ester of the flufenamic acid with methyl salicylate (N-m-trifluoromethyl-phenylanthranilate of O-methoxycarbonylphenyl, corresponding to the formula (1) for R=$CH_3$), hereinafter indicated as compound I, has been determined in the mouse in comparison with the flufenamic acid, the methyl salicylate and an equimolar mixture of flufenamic acid and methyl salicylate, by administering aqueous suspensions of the substances being tested; the results reported in the Table 1 show that the compound I is relevantly less toxic than the reference substances as well as than their mixture.

In the rat too the toxicity of compound I is very low (4,500 mg/kg).

The anti-inflammatory activity, as tested by the carragenin induced edema, on the contrary, is high and, in terms of molar doses, is like that of the flufenamic acid and higher than that of the methyl salicylate and that of the equimolar mixture of methyl salicylate and of flufenamic acid (Table 2).

The edema was induced by injecting the carrageenin (0.1 ml of the 1% suspension in physiological solution)

in the plantar aponeurosis of the rear paw of the rat one hour after the oral administration of the tested substances; the edema inhibition was evaluated, 3 to 4 hours after the carrageenin injection, from the difference between the volumes of the paw before and after the carragenin injection with respect to a group of control animals.

In a further series of experiments, the activity of the compound I has been evaluated with respect to the carrageenin induced edema in the rat in comparison with acetylsalicylic acid, phenylbutazone and aspirin; in this case 0.1 ml of a 1% carragenin solution in physiological medium was injected in the right rear paw, whereas in the left rear paw physiological solution was injected.

The volume difference between the two paws was compared with the values of a control group. In this case too, the carrageenin was injected one hour after the oral administration of the substances being tested as an aqueous suspension; the edema was evaluated 3 hours after the carrageenin injection.

The results are reported in Table 3; the activity is higher than that of aspirin and phenylbutazone, and lower than that of indomethacin.

The compound I has also been tested in the adjuvant induced arthritis in the rat, according to two different experimental models.

In the first one, relating to the developing arthritis (Table 4), groups of six Lewis rats have been tested for each dosage; a group was used as the control. Suspensions of the compound being tested were administered for 14 days, starting on the same day of the adjuvant inoculation (0.3 mg of Mycobacterium butyricum in 0.1 ml of mineral oil) in the plantar surface of the right rear paw. The body weights and the volumes of both paws were measured at the third and fourteenth days; the body weights were taken as the toxicity indexes; the paw volumes were used for the calculation of the percent inhibition of the swelling as determined by the adjuvant induced arthritis (D. Walz et al., J. Pharmacol. Exper. Therap., 178, 223, 1971).

The data of the Table 4 clearly show the strong inhibiting effect of the compound I in this experimental model. At the same time, the increase of the weight of the rats was normal, which is an index of poor toxicity. According to the second experimental model of adjuvant induced arthritis, there were studied the effects of the tested compounds in the disease already developed for 14 days; the substances were daily administered to groups of six rats for each dosage, from the 14th to the 18th day. The results are reported in table 5; in this test too, the compound I is more active than acetylsalicylic acid and than phenylbutazone. There was also investigated the irritating property of the compound with respect to the gastric tissues in the rat.

The substances were administered as an aqueous suspension and the animals ware sacrificed after either 4 or 24 hours; the stomachs were removed, opened, washed under tap water and examined.

The following score scale was used for the 24 hour test (Table 6):
0 = no lesion or hemorrhage
1 = one or two light lesions with hemorrhage
2 = some light lesions with hemorrhage
3 = some lesions with hemorrhage.
Pb 4 = very serious lesions with hemorrhage.

There were used three rats per each dosage and the sum of the scores was made.

As regards the 4 hour test (Table 7), the following scoring was used, relating to the hemorrhage degree:
0 = No hemorrhage
1 = one or two points of light hemorrhage
2 = some points of light hemorrhage
3 = some hemorrhages.
4 = very serious hemorrhages.

In this case too the sum of the scores of three rats for each dosage is reported.

It can be concluded that in both tests the compound I was highly less ulcerogenic than indomethacin and than acetylsalicylic acid.

The substances of the invention have consequently shown a high pharmacological activity as anti-inflammatory compounds, whereas their toxicity as well as their gastric irritating action are highly less than those of the reference drugs.

It is thus foreseeable their clinical use for the therapy of inflammatory states of different origin, particularly those of traumatic origin (even induced by heat or radiations), of infectious and rheumatic origin and in the other cases in which non-steroidal anti-inflammatory drugs are used, since there are not only combined but enhanced the therapeutical properties of the phenamates and those of the salicylic and acetylsalicylic derivatives. It is furthermore to be foreseen a clinical use thereof in the thrombotic diseases, through an action on the phenomena of aggregation and adhesion of the platelets.

The present compounds can be formulated, besides the forms for oral administration, such as tablets, capsules, pills, suspensions and the like, also in the form of suppositories for rectal use, in order to ensure either a systemic or a topic effect, or in the form of ovules for vaginal use, or in other forms for topic use, such as ointments, creams, sticks to be rubbed against the skin, medicated plasters and the like. In the pharmaceutical preparations the compounds of the present invention shall be combined with suitable excipients according to the known techniques for the preparations of these drugs.

In the preparations for systemic use, the present compounds shall be present in doses of between 100 mg and 1 g, whereas in the preparations for topic use the concentrations thereof shall be of between 5% and 50%.

TABLE 1

| Acute toxicity in the mouse per os | | |
|---|---|---|
| | Dose | |
| | mg/kg | mmoles/kg |
| Compound I | 9500 | 22.8 |
| Flufenamic acid | 875 | 3.1 |
| Methyl salicylate | 1155 | 7.6 |
| Equimolar mixture of methyl salicylate and flufenamic acid | 922 | 2.13 (of each component) |

TABLE 2

| Oral doses inhibiting by 50% the carragenin induced edema in the paw of rat | | |
|---|---|---|
| | Dose | |
| | mg/kg | mmoles/kg |
| Compound I | 176 | 0.42 |
| Flufenamic acid | 112 | 0.40 |
| Methyl salicylate | 289 | 1.9 |
| Equimolar mixture of methyl salicylate and flufenamic acid | 394* | 0.91 (of each component) |

*the inhibition for 394 mg/kg was 35%

TABLE 3

Inhibition of the carrageenin induced edema in the rat (comparison with acetylsalicylic acid, aspirin, phenylbutazone)

| | Dose, mg/kg os | Inhibition % | $ED_{30}$ (approximately) |
|---|---|---|---|
| Compound I | 50 | 52 | |
| | 25 | 42 | |
| | 10 | 34 | 8 mg/kg |
| | 5 | 21 | |
| | 1.5 | 24 | |
| | 1 | 0 | |
| Acetylsalicylic acid | 200 | 43 | |
| | 100 | 35 | |
| | 50 | 12 | |
| Phenylbutazone | 50 | 34 | |
| Indomethacin | 5 | 40 | |

N.B. $ED_{30}$ is the dose for which a 30% inhibition is obtained

TABLE 4

Adjuvant induced arthritis in the developing phase

| | Dose mg/kg os | Paw volume injected paw (3rd day) | Paw volume non injected paw (14th day) | Inhibition % injected paw (3rd day) | Inhibition % non injected paw (14th day) | Variation % body weight 3rd day | Variation % body weight 14th day |
|---|---|---|---|---|---|---|---|
| Compound I | 25 | 1.79 | 1.67 | 36 | 35 | + 36 | + 42 |
| | 10 | 1.53 | 1.47 | 53 | 47 | + 26 | + 34 |
| | 5 | 1.50 | 1.64 | 48 | 10 | + 24 | + 40 |
| Acetylsalicylic acid | 200 | 1.53 | 1.26 | 40 | 63 | + 12 | + 26 |
| | 100 | 1.65 | 1.49 | 30 | 33 | + 20 | + 34 |
| Phenylbutazone | 25 | 1.66 | 1.52 | 39 | 42 | + 23 | + 27 |
| Indomethacin | 1 | 1.63 | 1.55 | 39 | 32 | + 25 | + 29 |
| Control (with adjuvant) | — | 1.90 | 1.70 | — | — | + 24 | + 42 |

TABLE 5

Adjuvant induced arthritis, already developed

| | Dose mg/kg os | non injected paw, 18th day Volume | Inhibition % | Body weight % variation |
|---|---|---|---|---|
| Compound I | 25 | 1.04 | 100 | + 25 |
| | 10 | 1.82 | 46 | + 29 |
| | 5 | 2.16 | 27 | + 32 |
| Acetylsalicylic acid | 200 | 1.93 | 47 | + 32 |
| | 100 | 2.10 | 37 | + 34 |
| Phenylbutazone | 25 | 1.95 | 46 | + 30 |
| Indomethacin | 1 | 2.06 | 38 | + 37 |
| Control (with adjuvant) | — | 2.62 | — | + 35 |

TABLE 6

Acute gastric irritation in the rat (24 hours)

| | Dose mg/kg os | Score |
|---|---|---|
| Compound I | 1600 | 2 |
| | 800 | 3 |
| | 400 | 1 |
| | 200 | 1 |
| | 100 | 2 |
| | 50 | 1 |
| | 25 | 1 |
| Indomethacin | 40 | 5 |

TABLE 7

Acute gastric irritation in the rat (4 hours)

| | Dose mg/kg os | Score |
|---|---|---|
| Compound I | 1600 | 3 |
| | 800 | 2 |
| | 400 | 2 |
| | 200 | 2 |
| | 100 | 0 |

TABLE 7-continued

Acute gastric irritation in the rat (4 hours)

| | Dose mg/kg os | Score |
|---|---|---|
| | 50 | 0 |
| | 25 | 0 |
| Acetylsalicylic acid | 150 | 7 |

The following examples illustrate the preparation of the compounds of formula (1), but they must be only construed in the illustrative and not limiting sense.

EXAMPLE 1

A mixture of N-m-trifluoromethylphenylisatoic anhydride (200 g) and methyl salicylate (217 g) is heated to 180°–185° C. for 3 hours; the unreacted methyl salicylate is evaporated under reduced pressure (5 mm Hg).

By recrystallization from isopropanol there is obtained N-m-trifluoromethylphenyl anthranilate of O-methoxycarbonylphenyl, having melting point of 82°–83° C. If the reaction product is distilled under vacuum and cooled to low temperature, it can be obtained in a different polimorphic form, m.p. 39°–40° C.

The N-m-trifluoromethylphenylisatoic anhydride can be prepared by reacting phenyl chlorocarbonate (430 g) with flufenamic acid (300 g) in the presence of sodium bicarbonate (107 g) at 90°–95° C. for 2 hours; m.p. 120°–125° C.

EXAMPLE 2

By operating according to the Example 1, apart from the substitution of an equivalent amount of ethyl salicylate for the methyl salicylate, there is obtained the N-m-trifluoro-methyl-phenylanthranilate of O-ethoxycarbonylphenyl, m.p. 93°–95° C.

We claim:

1. N-m-trifluoromethylphenylanthranilate of O-alcoxy-carbonylphenyl, having the formula (1)

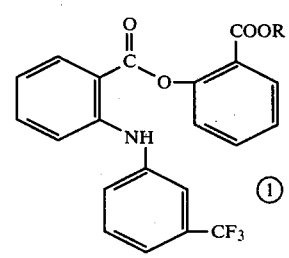

wherein R represents an alkyl group, preferably comprising 1 to 4 carbon atoms.

2. N-m-trifluoromethylphenylanthranilate of O-methoxycarbonylphenyl, according to claim 1.

3. N-m-trifluoromethylphenylanthranilate of O-ethoxycarbonylphenyl, according to claim 1.

4. An anti-inflammatory pharmaceutical composition containing an effective amount of a compound of claim 1 in combination with suitable vehicles and excipients.

5. A pharmaceutical composition according to claim 4, characterized in that the active ingredient is N-m-trifluoromethylphenylanthranilate of O-methoxycarbonylphenyl.

6. A pharmaceutical composition according to claim 4 or 5, characterized in that for the systemic used said active ingredient is present in a dosage of between 100 and 1000 mg.

7. A pharmaceutical composition according to claim 4 or 5, characterized in that for the topic use said active ingredient is present in an amount of between 5% and 50%.

* * * * *